United States Patent
Wu et al.

(10) Patent No.: US 11,180,752 B2
(45) Date of Patent: *Nov. 23, 2021

(54) DNA SEQUENCING USING HYDROGEL BEADS

(71) Applicant: Illumina, Inc., San Diego, CA (US)

(72) Inventors: Yir-Shyuan Wu, Albany, CA (US);
Filiz Gorpe-Yasar, Redwood City, CA (US); Tarun Kumar Khurana, Fremont, CA (US); Victoria Popic, San Francisco, CA (US); Erich B. Jaeger, San Francisco, CA (US); Mostafa Ronaghi, San Francisco, CA (US)

(73) Assignee: ILLUMINA, INC., San Diego, CA (US)

( * ) Notice: Subject to any disclaimer, the term of this patent is extended or adjusted under 35 U.S.C. 154(b) by 17 days.

This patent is subject to a terminal disclaimer.

(21) Appl. No.: 16/272,870

(22) Filed: Feb. 11, 2019

(65) Prior Publication Data

US 2019/0249171 A1    Aug. 15, 2019

Related U.S. Application Data

(60) Provisional application No. 62/630,175, filed on Feb. 13, 2018.

(51) Int. Cl.
*C12N 15/10* (2006.01)
*B01L 3/00* (2006.01)
(Continued)

(52) U.S. Cl.
CPC .......... *C12N 15/1068* (2013.01); *B01L 3/508* (2013.01); *B01L 7/52* (2013.01);
(Continued)

(58) Field of Classification Search
CPC ........ B01L 3/508; B01L 7/52; B01L 2200/16; B01L 2300/123; C12N 15/1068; C12Q 1/6806; C12Q 1/6834
See application file for complete search history.

(56) References Cited

U.S. PATENT DOCUMENTS 5,130,238 A    7/1992    Malek
5,185,243 A    2/1993    Ullman
(Continued)

FOREIGN PATENT DOCUMENTS

CA    3047328    6/2018
EP    0320308    6/1989
(Continued)

OTHER PUBLICATIONS

Rakszewska et al. (Angewandte Chemie, 2016, 55:6698-6701) (Year: 2016).*

(Continued)

*Primary Examiner* — Jeremy C Flinders
(74) *Attorney, Agent, or Firm* — Knobbe, Martens, Olson & Bear LLP

(57) ABSTRACT

Systems, methods, and compositions provided herein relate to preparation of beads encapsulating long DNA fragments for high-throughput spatial indexing. Some embodiments include preparation of nucleic acid libraries within the bead, wherein the bead includes pores that allow diffusion of reagents while retaining genetic material.

29 Claims, 13 Drawing Sheets
Specification includes a Sequence Listing.

(51) Int. Cl.
*C12Q 1/6834* (2018.01)
*C12Q 1/6806* (2018.01)
*B01L 7/00* (2006.01)

(52) U.S. Cl.
CPC ......... *C12Q 1/6806* (2013.01); *C12Q 1/6834* (2013.01); *B01L 2200/141* (2013.01); *B01L 2200/16* (2013.01); *B01L 2300/123* (2013.01)

(56) References Cited

U.S. PATENT DOCUMENTS

| | | |
|---|---|---|
| 5,455,166 A | 10/1995 | Walker |
| 5,573,907 A | 11/1996 | Carrino |
| 5,679,524 A | 10/1997 | Nikiforov |
| 5,958,451 A | 9/1999 | Chen |
| 6,210,891 B1 | 4/2001 | Nyren |
| 6,214,587 B1 | 4/2001 | Dattagupta |
| 6,258,568 B1 | 7/2001 | Nyren |
| 6,274,320 B1 | 8/2001 | Rothberg |
| 6,355,431 B1 | 3/2002 | Chee |
| 6,890,741 B2 | 5/2005 | Fan |
| 6,913,884 B2 | 7/2005 | Stuelpnagel |
| 7,001,792 B2 | 2/2006 | Sauer |
| 7,057,026 B2 | 6/2006 | Barnes |
| 7,115,400 B1 | 10/2006 | Adessi |
| 7,211,414 B2 | 5/2007 | Hardin |
| 7,244,559 B2 | 7/2007 | Rothberg |
| 7,315,019 B2 | 1/2008 | Turner |
| 7,329,492 B2 | 2/2008 | Hardin |
| 7,405,281 B2 | 7/2008 | Xu |
| 7,582,420 B2 | 9/2009 | Oliphant |
| 7,595,883 B1 | 9/2009 | Gamal |
| 7,611,869 B2 | 11/2009 | Fan |
| 7,670,810 B2 | 3/2010 | Gunderson |
| 7,985,565 B2 | 7/2011 | Mayer |
| 2005/0053980 A1 | 3/2005 | Gunderson |
| 2005/0181440 A1 | 8/2005 | Chee |
| 2005/0191698 A1 | 9/2005 | Chee |
| 2008/0108082 A1 | 5/2008 | Rank |
| 2009/0026082 A1 | 1/2009 | Rothberg |
| 2009/0127589 A1 | 5/2009 | Rothberg |
| 2009/0186349 A1 | 7/2009 | Gunderson |
| 2010/0137143 A1 | 6/2010 | Rothberg |
| 2010/0282617 A1 | 11/2010 | Rothberg |
| 2012/0129954 A1 | 5/2012 | Falcone et al. |
| 2015/0157569 A1 | 6/2015 | Shum et al. |
| 2015/0284768 A1 | 10/2015 | Craig et al. |
| 2015/0376609 A1 | 12/2015 | Hindson et al. |
| 2016/0271064 A1 | 9/2016 | Sell et al. |
| 2019/0249171 A1 | 8/2019 | Wu et al. |

FOREIGN PATENT DOCUMENTS

| | | |
|---|---|---|
| EP | 0336731 | 10/1989 |
| EP | 0439182 | 7/1991 |
| JP | 2016-517281 | 6/2016 |
| KR | 10-2017-0020704 | 2/2017 |
| RU | 2603745 | 11/2016 |
| WO | WO 1989/09835 | 10/1989 |
| WO | WO 1989/12696 | 12/1989 |
| WO | WO 1990/01069 | 2/1990 |
| WO | WO 1991/006678 A1 | 5/1991 |
| WO | WO 2004/018497 A2 | 3/2004 |
| WO | WO 2006/125458 A1 | 11/2006 |
| WO | WO 2007/123744 A2 | 11/2007 |
| WO | WO 2008/109176 | 9/2008 |
| WO | WO 2012/058096 A1 | 5/2012 |
| WO | WO 2014/145555 A1 | 9/2014 |
| WO | WO 2014/189957 | 11/2014 |
| WO | WO 2015/048173 | 4/2015 |
| WO | WO 2015/088299 | 6/2015 |
| WO | WO 2015/147147 | 10/2015 |
| WO | WO 2015/200893 | 12/2015 |
| WO | WO 2016/004234 | 1/2016 |
| WO | WO 2016/130704 | 8/2016 |
| WO | WO 2017/013138 | 1/2017 |
| WO | WO 2017/040024 | 3/2017 |
| WO | WO 2017/075265 | 5/2017 |
| WO | WO 2017/100347 | 6/2017 |
| WO | WO 2018/071448 | 4/2018 |
| WO | WO 2018/119301 | 6/2018 |
| WO | WO 2018/140966 | 8/2018 |
| WO | WO 2019/028047 | 2/2019 |
| WO | WO 2019/028166 | 2/2019 |
| WO | WO 2019/160820 | 8/2019 |

OTHER PUBLICATIONS

Bentley et al: Nature, 456, 53, 2008.
Cockroft et al: J Am Chem Soc, 130, 818, 2008.
Deamer et al: Trends Biotechnol, 18, 147, 2000.
Deamer et al: Acc Chem Res, 35, 817, 2002.
Korlach et al: Pnas, 105, 1176, 2008.
Lan Freeman et al: "Single-cell genome sequencing at ultra-high-throughput with microfluidic droplet barcoding, (includes Online Methods)", 1-7, 24-33, Nature Biotechnology, vol. 35, No. 7, Jul. 1, 2017 (Jul. 1, 2017) pp. 640-646, 4pp.
Levene et al: Science, 299, 682, 2003.
Li et al: Nat Mater, 2, 611, 2003.
Lundquist et al: Opt Lett, 33, 1026, 2008.
Ronaghi et al: Anal Biochem, 242(1), 84, 1996.
Ronaghi et al: Science, 281(5375), 363, 1998.
Ronaghi: Genome Res, 11(1), 3, 2001.
Soni et al: Clin Chem, 53, 1996, 2007.
Appleby et al. (Methods Mol Biol. 2009; 513:19-39).
Augst et al. Alginate hydrogels as biomaterials. Macromolecular Bioscience. 2006. 6: 623-633. (Year: 2006).
Bigdeli et al. A simple method for encapsulating single cells in alginate microspheres allows for direct PCR and whole genome amplification. PLoS One. 2015. 10(2): e011738. 15 pages. (Year: 2015).
Dean et al., Proc. Natl. Acad. Sci. USA 99:5261-66 (2002).
FOX et al. (Methods Mol Biol. 2009;553:79-108).
Garni, Biopores/membrane proteins in synthetic polymer membranes, Biochimica et Biophysica Acta, 1859, 2017, 619-638.
Grothues et al. Nucleic Acids Res. 21(5):1321-2 (1993).
Healy, Nanomed. 2, 459-481 (2007).
International Search Report and Written Opinion issued in patent application No. PCT/US2019/027540, dated Jul. 24, 2019.
International Search Report issued in application No. PCT/US2018/044855, dated Oct. 15, 2018.
Kumachev et al., "High-throughput generation of hydrogel microbeads with varying elasticity for cell encapsulation", Biomaterials, Elsevier Science Publishers BV., Barking, GB, (Feb. 1, 2011), pp. 1477-1483.
Lage et al., Genome Research 13:294-307 (2003).
Lizardi et al., Nat. Genet. 19:225-232 (1998).
Margulies et al. (Nature 2005 437: 376-80).
Morozova et al. (Genomics. 2008 92:255-64).
Novak et al., "Single-cell multiplex gene detection and sequencing with microfluidically generated agarose emulsions", Ange Chem Int Ed, 2011, 50, 390-395.
Picelli et al., "Tn5 transposase and tagmentation procedures for massively scaled sequencing projects", Genome Research, vol. 24, No. 12, Jul. 30, 2014 (Jul. 30, 2014), pp. 2033-2040.
Pregibon et al., "Optimization of Encoded Hydrogel Particles for Nucleic Acid Quantification", Analytical Chemistry, vol. 81, No. 12, Jun. 15, 2009 (Jun. 15, 2009), pp. 4873-4881.
Search Report issued in RU application No. 2019144343, dated Jun. 21, 2020.
Search Report and Written Opinion issued in application No. PCT/US2019/057852, dated Jan. 16, 2020.
Shendure et al. (Science 2005 309: 1728-32).
Tan et al., Heterogeneous multi-compartmental hydrogel particles as synthetic cells for incompatible tandem reactions, 2017, Nature Communications, 8,663, pp. 1-10 (Year: 2017).
Trivedi et al. Microfluidic encapsulation of cells in alginate capsules for high throughput screening. 31st Annual International Confer-

(56) References Cited

OTHER PUBLICATIONS ence of the IEEE EMBS. Minneapolis, Minnesota, USA. Sep. 2-6, 2009. 2009: 7037-7040. (Year: 2009).
Vitak et al. Nat Meth. 2017;14:302-308.
Walker et al., Nucl. Acids Res. 20:1691-96 (1992).
Decision to Grant issued in RU application No. 2019144343, dated Apr. 27, 2021.
Office Action issued in JP application No. 2019-568626, dated Feb. 2, 2021.
Shupletsova et al., "Encapsulation of cells and tissues of the pancreas: problems and ways to overcomethem", Genes and cells, volume XI, N 1, 2016, pp. 18-23.
Search Report issued in AU application No. 2019220559, dated Mar. 12, 2021.
Search Report issued in AU application No. 2019220559, dated May 19, 2021.
Search Report issued in AU application No. 2018312560, dated Mar. 11, 2021.
Office Action issued in EP application No. 18755643.6, dated May 10, 2021.
Office Action issued in JP application No. 2019-568626, dated Jun. 22, 2021.

\* cited by examiner

DNA SEQUENCING USING HYDROGEL BEADS

CROSS-REFERENCE TO RELATED APPLICATIONS

This application claims priority to U.S. Provisional Application No. 62/630,175, filed on Feb. 13, 2018, which is hereby incorporated by reference in its entirety.

REFERENCE TO SEQUENCE LISTING

The present application is being filed along with a Sequence Listing in electronic format. The Sequence Listing is provided as a file entitled Sequence_Listing_ILLINC_420A, created on Feb. 11, 2019, which is 987 bytes in size. The information in the electronic format of the Sequence Listing is incorporated herein by reference in its entirety.

FIELD

Systems, methods, and compositions provided herein relate to hydrogel beads, and methods of encapsulating long DNA within hydrogel beads, for use in determining the sequence of polynucleotides and related library preparation.

BACKGROUND

Next generation sequencers are powerful tools that generate large amounts of genomic data per sequencing run. Interpreting and analyzing this large amount of data can be challenging. Sequencing by synthesis (SBS) technology provides high quality sequencing data. However short reads (maximum read length is 2×300 bp) are one limitation of current SBS chemistry. Recently, there is increased emphasis on sequencing longer DNA molecules in order to better capture single nucleotide variants (SNP), insertion/deletion, and structural variants, and for improved genomic identification.

SUMMARY

Some embodiments provided herein relate to a hydrogel bead for performing DNA reactions. In some embodiments, the hydrogel bead includes a hydrogel polymer precursor, a crosslinker, and DNA disposed within the hydrogel bead. In some embodiments, the bead includes pores that allow diffusion of a reagent through the bead while retaining the DNA. In some embodiments, the DNA is a long DNA molecule of 50,000 base pairs or greater.

Some embodiments provided herein relate to a flow cell device for performing DNA sequencing. In some embodiments, the flow cell device includes a solid support. In some embodiments, the solid support includes a surface having a degradable hydrogel encapsulating DNA deposited thereon. In some embodiments, the degradable hydrogel includes pores that are sized to allow diffusion of a reagent through the hydrogel, but are too small to allow DNA to traverse the pores.

Some embodiments provided herein relate to a system for DNA sequencing. In some embodiments, the system includes a stage configured to hold a flow cell device, a flow cell device, and a detector for obtaining sequencing data.

Some embodiments provided herein relate to a method of sequencing DNA. In some embodiments, the method includes obtaining a bead encapsulating DNA as described herein. In some embodiments, the method includes providing a flow cell device described herein. In some embodiments, the method further includes amplifying DNA encapsulated within the hydrogel, performing a tagmentation reaction on the DNA encapsulated within the hydrogel, or sequencing the DNA. In some embodiments, the method further includes generating a DNA library encapsulated within the hydrogel.

BRIEF DESCRIPTION OF THE DRAWINGS

FIG. 7A shows the spatial reads for cells encapsulated within a hydrogel bead, and the inset depicts a micrograph showing a cell within the hydrogel bead. FIG. 7B shows the spatial reads for long DNA fragments encapsulated within a hydrogel bead, and the inset depicts a micrograph showing the fragments encapsulated within the beads.

DETAILED DESCRIPTION

Figure 1A:
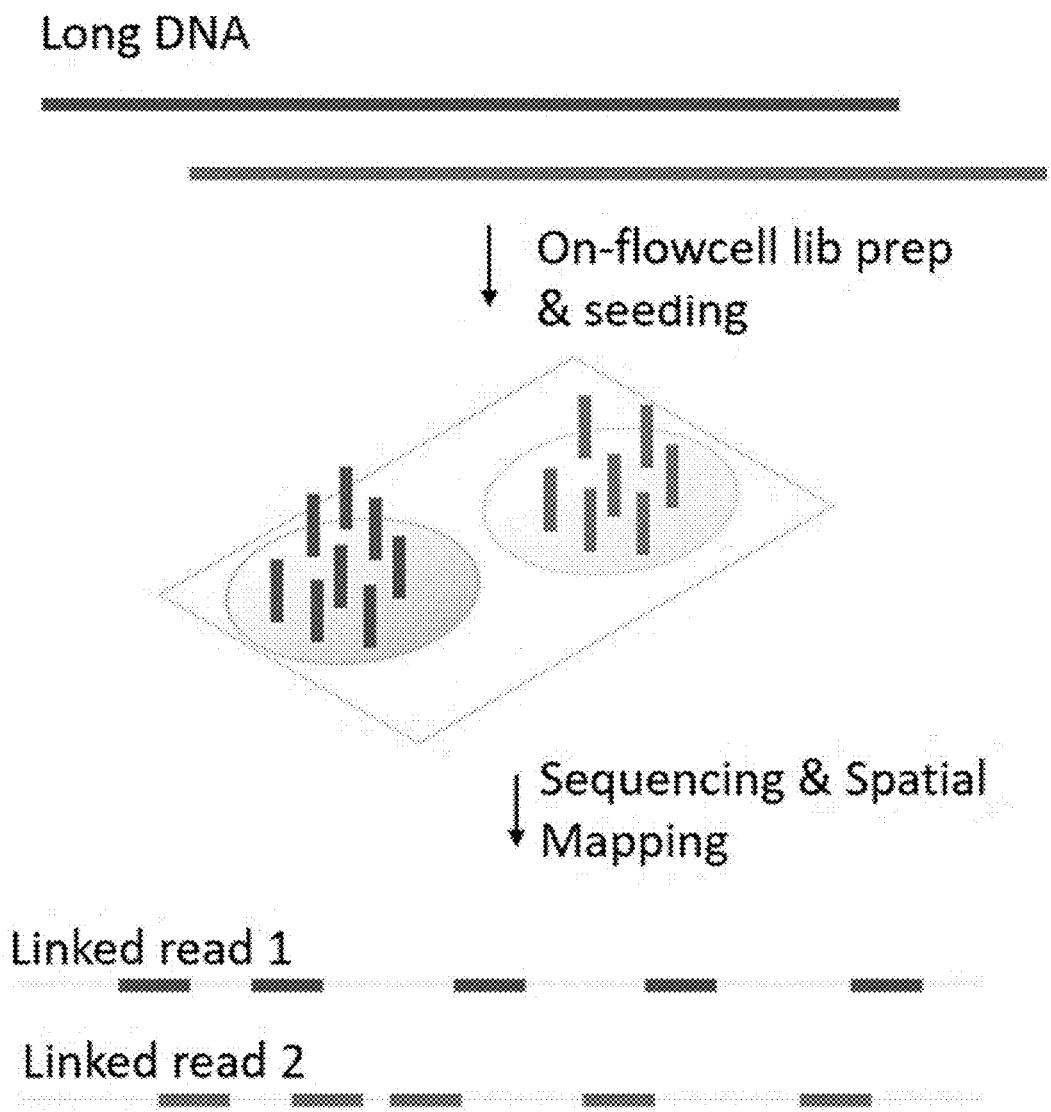
FIG. 1A is a schematic that illustrates an embodiment for spatial indexing of long DNA by on-flow cell library preparation and seeding.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Embodiments relate to compositions, systems, and methods for encapsulating long DNA fragments into beads to determine the nucleotide sequence of the DNA fragments. This allows creation of reliable and high-throughput methods of sequencing relatively long DNA fragments, as described below. The methods and systems described herein relate to sequencing of long DNA fragments encapsulated in a single bead, enabling improved sequencing and identification of genomic DNA. In some embodiments, the method includes encapsulating a sample of DNA fragments within a hydrogel bead, loading the hydrogel beads encapsulating the sample of DNA fragments on a flow cell device, preparing a library, releasing the prepared library on a surface of the flow cell device, and clustering and sequencing the released library.

In some embodiments, preparing a library includes tagmentation of the encapsulated DNA. Tagmentation of the encapsulated DNA cleaves longer DNA sequences into shorter tagmentation fragments which are then used to generate clusters of DNA on a surface of the flowcell. A cluster is a product of a tagmentation fragment of the long DNA, each of which can be sequenced using SBS sequencing, for example. A group of clusters from a single long DNA molecule is referred to herein as a long DNA island. In some embodiments, a single hydrogel bead may encapsulate a single long DNA molecule or multiple long DNA molecules. Each long DNA molecule generates a single long DNA island. The clusters of all long DNA islands within a single hydrogel bead is referred to herein as a cluster cloud. Thus, a cluster cloud represents all clusters within a single hydrogel bead, and may include many long DNA islands (each long DNA island representing a single long DNA molecule), and each long DNA island includes multiple clusters.

The beads may include hydrogel polymers and cross-linkers that are mixed in the presence of a long DNA molecule, or a source containing a long DNA molecule, which then form hydrogel beads encapsulating the DNA molecule. In some embodiments, the long DNA source is a cell. The hydrogel beads may include pores that allow diffusion of reagents through the hydrogel bead while retaining the long DNA within the bead, thereby allowing reactions to take place within each of the beads.

Some embodiments include methods of using the beads encapsulating long DNA to perform nucleic acid reactions, including for example, high-throughput spatial indexing of long DNA molecules. As shown in FIG. 1A, library preparation from a long DNA molecule may be readily prepared by clustering and seeding the clusters from a single long DNA molecule as a "cluster patch" on the surface, which can then be read and spatially mapped. As used herein, the term "long DNA" can include DNA fragments that are greater than 300 base pairs. Long DNA fragments, as used herein, refers to DNA of a length of great than 1 kb, 2.5 kb, 5 kb, or more, such as 10, 15, 20, 25, 30, 35, 40, 45, 50, 60, 70, 80, 90, 100, 200, 300, 400, or 500 kb, or more, including an amount within a range defined by any two of the aforementioned values.

Without being bound by theory, the methods, systems, and compositions provided herein include several advantages over current library preparation techniques. For example, in some embodiments, the methods allow sample preparation in a single bead to be used to fragment a genomic sample into a series of long DNA fragments. That single bead can then be adhered to one special location on a flow cell where the long DNA fragments are deposited such that each of the long DNA fragments are positioned adjacent one another on the flow cell surface. The system then determines the nucleotide sequence from each long DNA fragment. Since they are adjacent one another on the flow cell surface, the system may use this spatial location data to more efficiently reconstruct the final sequence of the original genomic DNA. The system may deposit spatially co-located reads directly from single cells, long DNA fragments, or chromosomes. In some embodiments, the methods allow for low input, PCR-free workflow for library preparation. In some embodiments, the methods may be performed without a need for molecular barcoding. In some embodiments, the methods allow simplified workflow automation. In some embodiments, the methods are compatible with a variety of nucleic acid assays and workflows.

Some embodiments relate to methods of preparing a hydrogel bead that encapsulates long DNA. In some embodiments, the hydrogel bead encapsulating long DNA can be used to process the cellular genome and perform DNA library preparation inside the bead. In some embodiments, the hydrogel bead encapsulating a long DNA fragment encapsulates a single cell, which can be used to process the cellular genomic DNA, and to perform whole DNA library preparation inside the bead.

In some embodiments, the pore size of the hydrogel bead can be engineered to allow the diffusion of enzymes, chemicals, and smaller sized primers (<50 bps), while retaining larger nucleic acids (>300 bps) such that the long DNA fragments and the produced DNA library may be retained inside the hydrogel beads during processing. In some embodiments, specific primers can be chemically linked within the hydrogel bead matrix to hybridize and process specific genomic DNA. The DNA library from a single cell can then be released to a specific area, for example, on flow cell surface for library seeding. Subsequently, this results in a spatial distribution of "DNA clusters" on the flow cell originating from the encapsulated long DNA fragments, thus simplifying the read alignment during post processing.

As used herein, the term "reagent" describes an agent or a mixture of two or more agents useful for reacting with, interacting with, diluting, or adding to a sample, and may include agents used in nucleic acid reactions, including, for example buffers, chemicals, enzymes, polymerase, primers having a size of less than 50 base pairs, template nucleic acids, nucleotides, labels, dyes, or nucleases. In some embodiments, the reagent includes lysozyme, proteinase K, random hexamers, polymerase (for example, 129 DNA polymerase, Taq polymerase, Bsu polymerase), transposase (for example, Tn5), primers (for example, P5 and P7 adaptor sequences), ligase, catalyzing enzyme, deoxynucleotide triphosphates, buffers, or divalent cations.

Hydrogel Beads Encapsulating Genetic Material

One embodiment includes a bead including a hydrogel polymer and genetic material. As used herein, the term "hydrogel" refers to a substance formed when an organic polymer (natural or synthetic) is cross-linked via covalent, ionic, or hydrogen bonds to create a three-dimensional open-lattice structure that entraps water molecules to form a gel. In some embodiments, the hydrogel may be a biocompatible hydrogel. As used herein, the term "biocompatible hydrogel" refers to a polymer that forms a gel that is not toxic to living cells and allows sufficient diffusion of oxygen and nutrients to entrapped cells to maintain viability. In some embodiments, the hydrogel polymer includes 60-90% fluid, such as water, and 10-30% polymer. In certain embodiments, the water content of hydrogel is about 70-80%.

Hydrogels may be prepared by cross-linking hydrophilic biopolymers or synthetic polymers. Thus, in some embodiments, the hydrogel may include a crosslinker. As used herein, the term "crosslinker" refers to a molecule that can form a three-dimensional network when reacted with the appropriate base monomers. Examples of the hydrogel polymers, which may include one or more crosslinkers, include but are not limited to, hyaluronans, chitosans, agar, heparin, sulfate, cellulose, alginates (including alginate sulfate), collagen, dextrans (including dextran sulfate), pectin, carrageenan, polylysine, gelatins (including gelatin type A), agarose, (meth)acrylate-oligolactide-PEO-oligolactide-(meth)acrylate, PEO—PPO-PEO copolymers (Pluronics), poly(phosphazene), poly(methacrylates), poly(N-vinylpyrrolidone), PL(G)A-PEO-PL(G)A copolymers, poly(ethylene imine), polyethylene glycol (PEG)-thiol, PEG-acrylate, acrylamide, N,N'-bis(acryloyl)cystamine, PEG, polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), bisacrylamide, diacrylate, diallylamine, triallylamine, divinyl sulfone, diethyleneglycol diallyl ether, ethyleneglycol diacrylate, polymethyleneglycol diacrylate, polyethyleneglycol diacrylate, trimethylopropoane trimethacrylate, ethoxylated trimethylol triacrylate, or ethoxylated pentaerythritol tetracrylate, or combinations thereof. Thus, for example, a combination may include a polymer and a crosslinker, for example polyethylene glycol (PEG)-thiol/PEG-acrylate, acrylamide/N,N'-bis(acryloyl)cystamine (BACy), or PEG/polypropylene oxide (PPO).

In some embodiments, a crosslinker forms a disulfide bond in the hydrogel polymer, thereby linking hydrogel polymers. In some embodiments, the hydrogel polymers form a hydrogel matrix having pores (for example, a porous hydrogel matrix). These pores are capable of retaining sufficiently large genetic material within the hydrogel bead, for example, long DNA fragments, but allow small materials, such as reagents, to pass through the pores, thereby passing in and out of the hydrogel beads. In some embodiments, the pore size is finely tuned by varying the ratio of the concentration of polymer to the concentration of crosslinker. In some embodiments, the ratio of polymer to crosslinker is 30:1, 25:1, 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:15, 1:20, or 1:30, or a ratio within a range defined by any two of the aforementioned ratios. In some embodiments, additional functions such as DNA primer, or charged chemical groups can be grafted to polymer matrix to meet the requirements of different applications.

As used herein, the term "porosity" means the fractional volume (dimension-less) of a hydrogel that is composed of open space, for example, pores or other openings. Therefore, porosity measures void spaces in a material and is a fraction of volume of voids over the total volume, as a percentage between 0 and 100% (or between 0 and 1). Porosity of the hydrogel may range from 0.5 to 0.99, from about 0.75 to about 0.99, or from about 0.8 to about 0.95.

The hydrogels can have any pore size. As used herein, the term "pore size" refers to a diameter or an effective diameter of a cross-section of the pores. The term "pore size" can also refer to an average diameter or an average effective diameter of a cross-section of the pores, based on the measurements of a plurality of pores. The effective diameter of a cross-section that is not circular equals the diameter of a circular cross-section that has the same cross-sectional area as that of the non-circular cross-section. In some embodiments, the hydrogel can be swollen when the hydrogel is hydrated. The sizes of the pores size can then change depending on the water content in the hydrogel. In some embodiments, the pores of the hydrogel can have a pore of sufficient size to retain genetic material within the hydrogel but allow reagents to pass through.

In some embodiments, the crosslinker is a reversible crosslinker. In some embodiments, a reversible crosslinker is capable of reversibly crosslinking the hydrogel polymer and is capable of being un-crosslinked in the presence of a cleaver. In some embodiments, a crosslinker can be cleaved by the presence of a reducing agent, by elevated temperature, or by an electric field. In some embodiments, the reversible crosslinker may be N,N'-bis(acryloyl)cystamine, a reversible crosslinker for polyacrylamide gels, wherein a disulfide linkage may be broken in the presence of a suitable reducing agent. In some embodiments, contacting the crosslinker with a reducing agent cleaves the disulfide bonds of the crosslinker, breaking down the hydrogel beads. The hydrogel beads degrade, and release the contents, such as nucleic acids that were retained therein. In some embodiments, the crosslinker is cleaved by increasing the temperature to greater than 50, 55, 60, 65, 70, 75, 80, 85, 90, 95, or 100° C. In some embodiments, the crosslinker is cleaved by contacting the hydrogel beads with a reducing agent. In some embodiments, the reducing agents include phosphine compounds, water soluble phosphines, nitrogen containing phosphines and salts and derivatives thereof, dithioerythritol (DTE), dithiothreitol (DTT) (cis and trans isomers, respectively, of 2,3-dihydroxy-1,4-dithiolbutane), 2-mercaptoethanol or 3-mercaptoethanol (BME), 2-mercaptoethanol or aminoethanethiol, glutathione, thioglycolate or thioglycolic acid, 2,3-dimercaptopropanol, tris(2-carboxyethyl)phosphine (TCEP), tris(hydroxymethyl)phosphine (THP), or P-[tris(hydroxymethyl)phosphine] propionic acid (THPP).

In some embodiments, elevating the temperature to increase diffusion or contacting with a reducing agent degrades the crosslinker, thereby releasing encapsulated genetic material from the hydrogel bead.

Figure 1B:
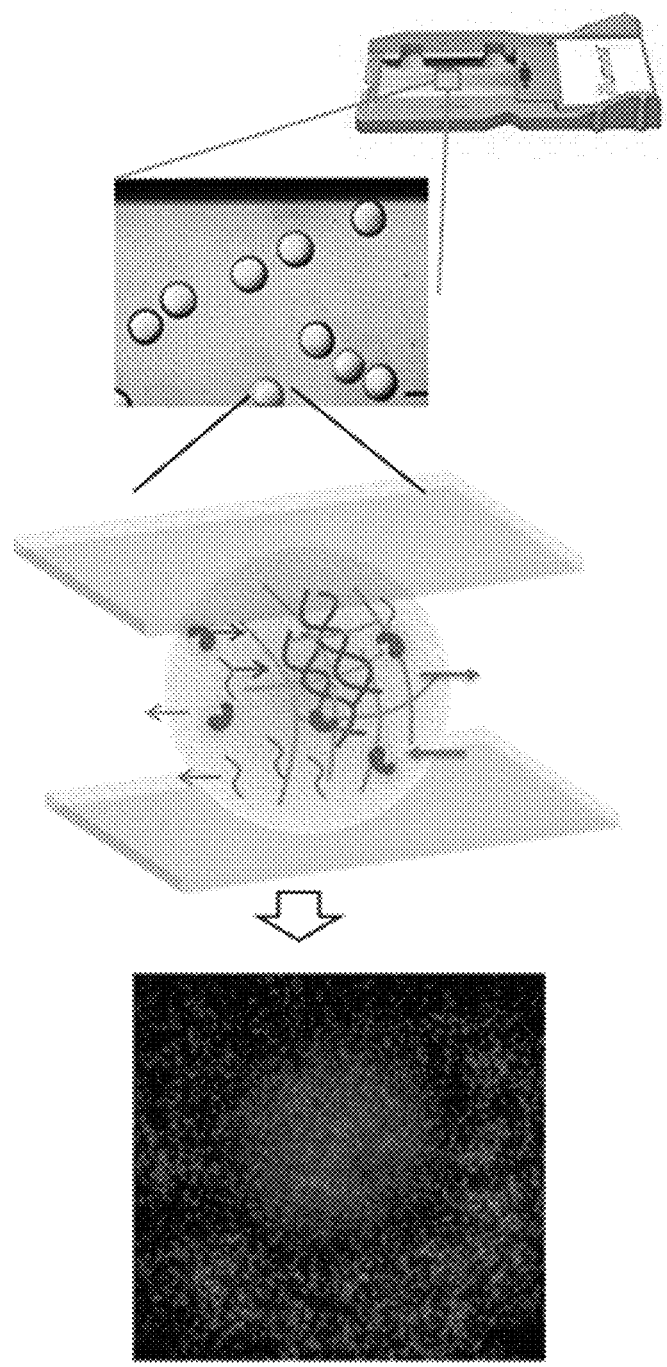
FIG. 1B is a schematic that illustrates spatial indexing using hydrogel beads that encapsulate long DNA molecules. Reagents may be used on the hydrogel beads to spatially generate a library on a flow cell surface.

In some embodiments, the crosslinking of the crosslinker establishes pores within the hydrogel bead. In some embodiments, the size of the pores in the hydrogel beads are regulatable and are formulated to encapsulate genetic material, such as DNA fragments of greater than about 5000 base pairs, but to allow smaller particles, such as reagents, or smaller sized nucleic acids of less than about 50 base pairs, such as primers, to pass through the pores, as shown in FIG. 1B. In some embodiments, the reagents including reagents for processing genetic material, such as reagents for isolating nucleic acids from a cell, for amplifying, barcoding, or sequencing nucleic acids, or for preparation of nucleic acid libraries. In some embodiments, reagents include, for example, lysozyme, proteinase K, random hexamers, polymerase (for example, Φ29 DNA polymerase, Taq polymerase, Bsu polymerase), transposase (for example, Tn5), primers (for example, P5 and P7 adaptor sequences), ligase, catalyzing enzyme, deoxynucleotide triphosphates, buffers, or divalent cations.

Figure 7A:
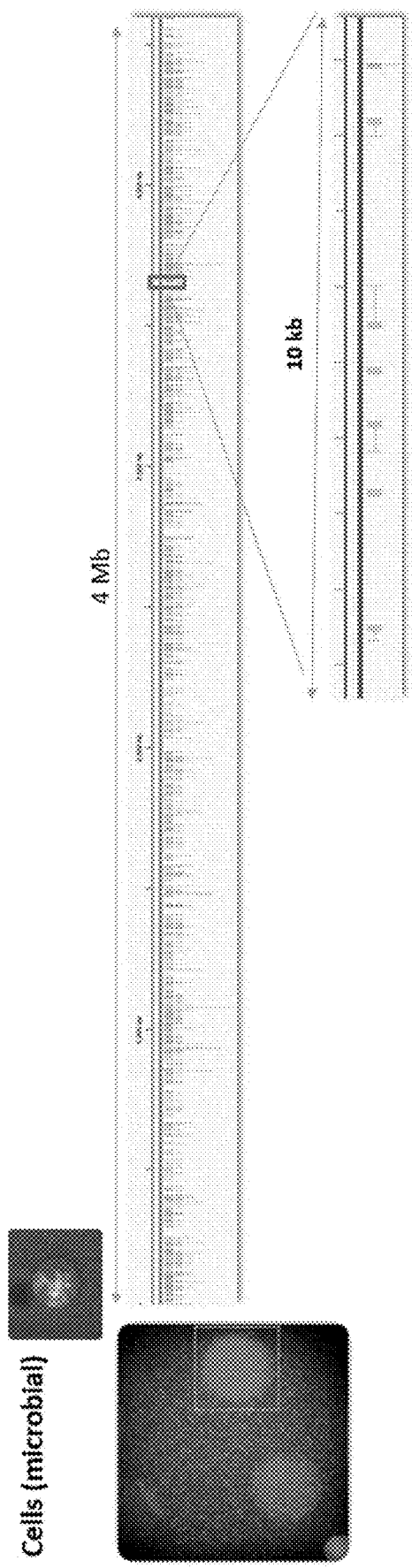
FIGS. 7A and 7B depict line graphs of spatial reads for long DNA encapsulated within a hydrogel bead.
Figure 7B:
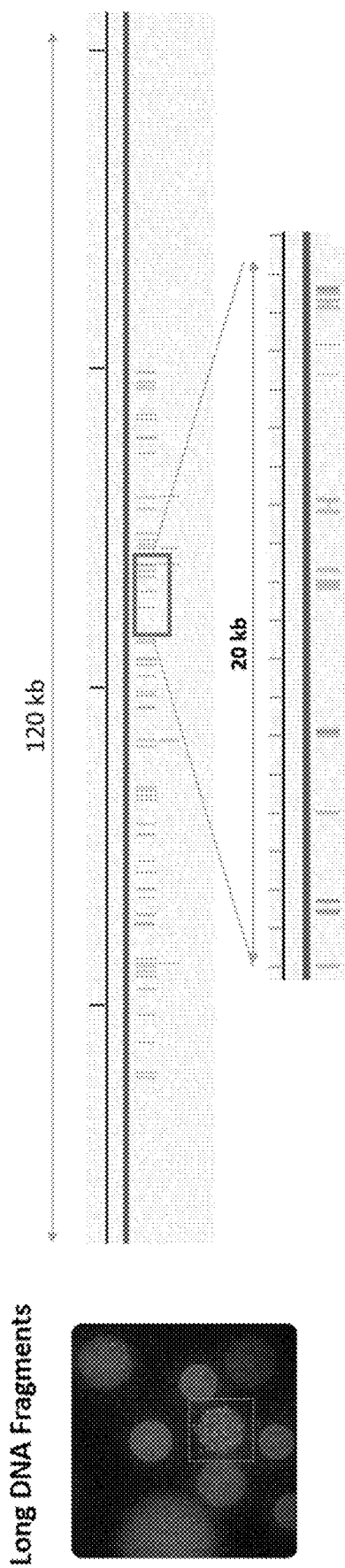

In some embodiments, the long DNA includes genomic DNA, viral nucleic acids, bacterial nucleic acids, or mammalian nucleic acids. In some embodiments, the hydrogel beads include a source of long DNA, including, for example a cell. In some embodiments, the cell is a single cell, including a prokaryotic or a eukaryotic cell. In some embodiments, the cell is a mammalian cell. In some embodiments, the cell is a human cell. In some embodiments, the cell is a bacterial cell. Thus, as shown in FIGS. 7A and 7B, the method may be performed on long DNA fragments or on cells, either or both of which is encapsulated with a hydrogel bead.

Methods of Making Beads

Some embodiments provided herein relate to methods of making beads that encapsulate long DNA fragments. In some embodiments, a hydrogel bead is prepared by vortex assisted emulsion. As used herein, vortex assisted emulsion refers to vortexing a hydrogel polymer with long DNA fragments or a source of long DNA fragments in a container, such as in a tube, vial, or reaction vessel. The components can be mixed, for example by manual or mechanical vortexing or shaking. In some embodiments, manual mixing results in hydrogel beads that encapsulate genetic material having a size of 2, 3, 4, 5, 10, 15, 20, 25, 30, 35, 40, 45, 50, 55, 60, 65, 70, 75, 80, 85, 90, 95, 100, 110, 120, 130, 140, or 150 μm in diameter, or a size within a range defined by any two of the aforementioned values. In some embodiments, the size of the beads is non-uniform, and thus, the size of the beads includes beads of various diameters.

In some embodiments, the beads are prepared by microfluidic droplet generation. As shown in FIG. 1B, microfluidic droplet generation includes use of a microfluidic device for assisted gel emulsion generation. In some embodiments, the microfluidic device includes microchannels configured to produce a hydrogel bead of a desired size and configured to encapsulate a selected amount of genetic material per bead. In some embodiments, the microfluidic device has a height of 50, 60, 70, 80, 90, 100, 110, 120, 130, 140, 150, 160, 170, 180, 190, or 200 μm, or a height within a range defined by any two of the aforementioned values. In some embodiments, the microfluidic device includes one or more channels. In some embodiments, the microfluidic device includes a channel for an aqueous stream and a channel for an immiscible fluid. In some embodiments, the width of the one or more channels is identical. In some embodiments, the width of the one or more channels is different. In some embodiments, the width of the one or more channels is 20, 30, 40, 45, 50, 55, 60, 65, 70, 75, 80, 85, 90, 95, 100, 105, 110, 115, 120, 125, 130, 135, 140, 145, or 150 μm, or a width within a range defined by any two of the aforementioned values. In some embodiments, the width of the aqueous channel is 75 μm. In some embodiments, the width of the immiscible fluid channel is 78 μm. One of skill in the art will recognize that the width can vary to finely tune the size of the bead. In addition to the size of the microfluidic device and the width of the channels, the flow rate of the aqueous channel and the immiscible fluid channel may also affect the size of the hydrogel beads.

In some embodiments, the flow rate of the solution in the aqueous phase channel is 1, 2, 5, 10, 20, 30, 40, 50, 60, 70, 80, 90, 100, 110, 120, 130, 140, or 150 μL/min, or a rate within a range defined by any two of the aforementioned values. In some embodiments, the flow rate of the immiscible fluid in the immiscible fluid channel is 20, 30, 50, 80, 100, 150, 160, 170, 180, 190, 200, 225, 250, 275, 300, 325, 350, 375, or 400 μL/min, or a rate within a range defined by any two of the aforementioned values. In some embodiments, the solution in the aqueous phase includes a hydrogel polymer, a crosslinker, and genetic material, which flows through an aqueous channel into an immiscible fluid, such as a carrier oil, at a flow rate less than the flow rate of the immiscible fluid, thereby forming droplets. In some embodiments, the immiscible fluid is oil, such as mineral oil, a hydrocarbon oil, a silicon oil, or a polydimethylsiloxane oil, or mixtures thereof. In some embodiments, the hydrogel droplets containing genetic material are formulated in a uniform size distribution. In some embodiments, the size of the hydrogel beads is finely tuned by adjusting the size of the microfluidic device, the size of the one or more channels, or the flow rate of either or both of the aqueous solution or immiscible fluid. In some embodiments, the resulting hydrogel bead has a diameter ranging from 2 to 150 μm, for example, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, or 150 μm, or a diameter within a range defined by any two of the aforementioned values.

In some embodiments, the size and uniformity of the hydrogel bead encapsulating genetic material can be further controlled by contacting hydrogel polymer prior to bead formation with a fluidic modifier, such as with an alcohol, including isopropyl alcohol.

In some embodiments, the amount of long DNA fragments encapsulated within a bead can be controlled by diluting or concentrating the long DNA fragments within the inputted sample. The sample including the long DNA fragments is mixed with hydrogel polymer, and the hydrogel polymer containing the long DNA fragments is submitted to vortex assisted emulsion or microfluidic droplet generation, as described herein.

In some embodiments, the hydrogel beads are functionalized with a nucleotide. In some embodiments, the nucleotide is an oligonucleotide or polyT nucleotide. In some embodiments, the nucleotide is bound to the hydrogel bead, and the functionalized bead can be used for targeted capture of a nucleotide of interest.

Methods of Processing Long DNA Fragments within Hydrogel Beads

Figure 2:
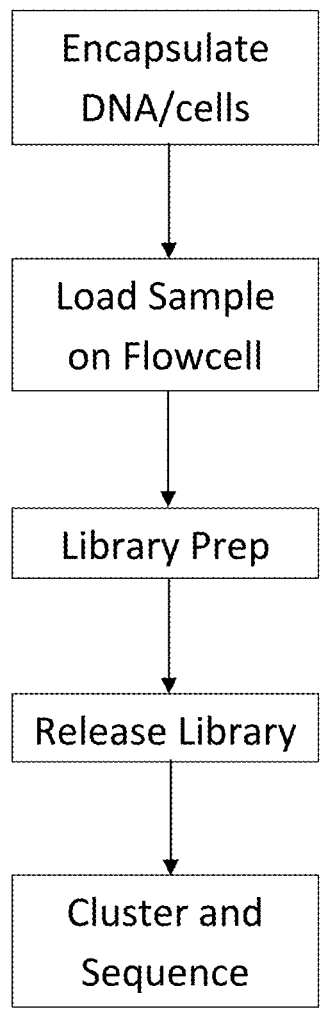
FIG. 2 is a flow diagram that depicts a method of encapsulating long DNA within a hydrogel bead, and preparing a library within the hydrogel bead, which can be clustered and sequenced on a flow cell device.

Some embodiments include methods of processing long DNA fragments within a bead as shown in FIG. 2, which depicts a flow diagram for preparing and processing long DNA molecules in a hydrogel bead. In a first step, a DNA sample, such as from genomic data or a cell is encapsulated within a hydrogel bead. In some embodiments, the long DNA fragment is retained within the hydrogel beads, and reagents are able to pass through the pores of the hydrogel beads. In some embodiments, reagents can include lysis agents, nucleic acid purification agents, tagmentation agents, PCR agents, or other agents used in processing of genetic materials. Thus, the hydrogel beads provide a microenvironment for controlled reactions of long DNA fragments within the hydrogel beads by allowing a barrier for reagents to pass in and out of the hydrogel beads, while retaining the long DNA fragments within the beads. Once the DNA is encapsulated into the beads, the process moves to the next step where the sample can be loaded into a flow cell to create the long DNA fragments through the library preparation process.

As used herein, the term "tagmentation" refers to the modification of DNA by a transposome complex comprising transposase enzyme complexed with adaptors comprising transposon end sequence. Tagmentation results in the simultaneous fragmentation of the DNA and ligation of the adaptors to the 5' ends of both strands of duplex fragments. Following a purification step to remove the transposase enzyme, additional sequences can be added to the ends of the adapted fragments, for example by PCR, ligation, or any other suitable methodology known to those of skill in the art.

In some embodiments, entire DNA library preparation can be accomplished seamlessly inside the hydrogel beads bound to the flow cell with multiple reagent exchanges by passing through the porous hydrogel while retaining the gDNA and its library products within the hydrogel matrix. The hydrogel may be resistant to high temperatures up to 95° C. for several hours to support different biochemical reactions.

In the next step in the process, the hydrogel bead encapsulating the long DNA fragments from the prior library preparation is treated to release, purify and isolate the long DNA fragments from the bead. Thus, for example the hydrogel bead is contacted with a lysis buffer. As used herein, "lysis" means perturbation or alteration to a cell wall or viral particle facilitating access to or release of the cellular RNA or DNA. Neither complete disruption nor breakage of the cell wall is an essential requirement for lysis. By the term "lysis buffer" is meant a buffer that contains at least one lysing agent. Typical enzymatic lysing agents include, but are not limited to, lysozyme, glucolase, zymolose, lyticase, proteinase K, proteinase E, and viral endolysins and exolysins. Thus, for example, lysis of cells in the beads may be performed by introducing lysing agents, such as lysozyme and proteinase K into the hydrogel beads. The gDNA from the cells is now contained within the beads. In some embodiments, following lysis treatment, isolated nucleic acid is retained within the hydrogel bead, and may be used for further processing.

As used herein, the terms "isolated," "to isolate," "isolation," "purified," "to purify," "purification," and grammatical equivalents thereof as used herein, unless specified otherwise, refer to the reduction in the amount of at least one contaminant (such as protein and/or nucleic acid sequence) from a sample or from a source (e.g., a cell) from which the material is isolated. Thus purification results in an "enrichment," for example, an increase in the amount of a desirable protein and/or nucleic acid sequence in the sample.

In some embodiments, the encapsulated nucleic acids are sequenced in full or in part within the hydrogel beads. The encapsulated nucleic acids can be sequenced according to any suitable sequencing methodology, such as direct sequencing, including sequencing by synthesis, sequencing by ligation, sequencing by hybridization, nanopore sequencing and the like.

Some embodiments provided herein relate to sequencing-by-synthesis (SBS) enabled for long DNA fragments. In SBS, extension of a nucleic acid primer along a nucleic acid template (e.g. a target nucleic acid or amplicon thereof) is monitored to determine the sequence of nucleotides in the template. The underlying chemical process can be polymerization (e.g. as catalyzed by a polymerase enzyme). In a particular polymerase-based SBS embodiment, fluorescently labeled nucleotides are added to a primer (thereby extending the primer) in a template dependent fashion such that detection of the order and type of nucleotides added to the primer can be used to determine the sequence of the template.

One or more amplified encapsulated nucleic acids can be subjected to an SBS or other detection technique that involves repeated delivery of reagents in cycles. For example, to initiate a first SBS cycle, one or more labeled nucleotides, DNA polymerase, etc., can be flowed into/through a hydrogel bead that houses one or more amplified nucleic acid molecules. Those sites where primer extension causes a labeled nucleotide to be incorporated can be detected. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use with amplicons produced by the methods of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., Analytical Biochemistry 242(1), 84-9 (1996); Ronaghi, Genome Res. 11(1), 3-11 (2001); Ronaghi et al. Science 281(5375), 363 (1998); U.S. Pat. Nos. 6,210,891; 6,258,568 and 6,274,320, each of which is incorporated herein by reference). In pyrosequencing, released PPi can be detected by being immediately converted to adenosine triphosphate (ATP) by ATP sulfurylase, and the level of ATP generated can be detected via luciferase-produced photons. Thus, the sequencing reaction can be monitored via a luminescence detection system. Excitation radiation sources used for fluorescence based detection systems are not necessary for pyrosequencing procedures. Useful fluidic systems, detectors and procedures that can be adapted for application of pyrosequencing to amplicons produced according to the present disclosure are described, for example, in WIPO Pat. App. Ser. No. PCT/US11/57111, US 2005/0191698 A1, U.S. Pat. Nos. 7,595,883, and 7,244,559, each of which is incorporated herein by reference.

Some embodiments can utilize methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zero mode waveguides (ZMWs). Techniques and reagents for FRET-based sequencing are described, for example, in Levene et al. Science 299, 682-686 (2003); Lundquist et al. Opt. Lett. 33, 1026-1028 (2008); Korlach et al. Proc. Natl. Acad. Sci. USA 105, 1176-1181 (2008), the disclosures of which are incorporated herein by reference.

Some SBS embodiments include detection of a proton released upon incorporation of a nucleotide into an extension product. For example, sequencing based on detection of released protons can use an electrical detector and associated techniques that are commercially available. Examples of such sequencing systems are pyrosequencing (e.g. commercially available platform from 454 Life Sciences a subsidiary of Roche), sequencing using γ-phosphate-labeled nucleotides (e.g. commercially available platform from Pacific Biosciences) and sequencing using proton detection (e.g. commercially available platform from Ion Torrent subsidiary of Life Technologies) or sequencing methods and systems described in US 2009/0026082 A1; US 2009/0127589 A1; US 2010/0137143 A1; or US 2010/0282617 A1, each of which is incorporated herein by reference. Methods set forth herein for amplifying target nucleic acids using kinetic exclusion can be readily applied to substrates used for detecting protons. More specifically, methods set forth herein can be used to produce clonal populations of amplicons that are used to detect protons.

Another sequencing technique is nanopore sequencing (see, for example, Deamer et al. Trends Biotechnol. 18, 147-151 (2000); Deamer et al. Acc. Chem. Res. 35:817-825 (2002); Li et al. Nat. Mater. 2:611-615 (2003), the disclosures of which are incorporated herein by reference). In some nanopore embodiments, the target nucleic acid or individual nucleotides removed from a target nucleic acid pass through a nanopore. As the nucleic acid or nucleotide passes through the nanopore, each nucleotide type can be identified by measuring fluctuations in the electrical conductance of the pore. (U.S. Pat. No. 7,001,792; Soni et al. Clin. Chem. 53, 1996-2001 (2007); Healy, Nanomed. 2, 459-481 (2007); Cockroft et al. J. Am. Chem. Soc. 130, 818-820 (2008), the disclosures of which are incorporated herein by reference).

Exemplary methods for array-based expression and genotyping analysis that can be applied to detection according to the present disclosure are described in U.S. Pat. Nos. 7,582,420; 6,890,741; 6,913,884 or 6,355,431 or US Pat. Pub. Nos. 2005/0053980 A1; 2009/0186349 A1 or US 2005/0181440 A1, each of which is incorporated herein by reference.

In the methods of isolating nucleic acids, amplification, and sequencing as described herein, various reagents are used for nucleic acid isolation and preparation. Such reagents may include, for example, lysozyme, proteinase K, random hexamers, polymerase (for example, Φ29 DNA polymerase, Taq polymerase, Bsu polymerase), transposase (for example, Tn5), primers (for example, P5 and P7 adaptor sequences), ligase, catalyzing enzyme, deoxynucleotide triphosphates, buffers, or divalent cations. These reagents pass through the pores of the hydrogel beads, whereas the genetic material is retained within the hydrogel beads. An advantage of the methods set forth herein is that they provide for an encapsulated microenvironment for the processing of nucleic acids within a hydrogel bead. This enables single cell processing for rapid and efficient processing of a target nucleic acid.

Adaptors can include sequencing primer sites, amplification primer sites, and indexes. As used herein an "index" can include a sequence of nucleotides that can be used as a molecular identifier and/or barcode to tag a nucleic acid, and/or to identify the source of a nucleic acid. In some embodiments, an index can be used to identify a single nucleic acid, or a subpopulation of nucleic acids. In some embodiments, nucleic acid libraries can be prepared within a hydrogel bead. In some embodiments, a single cell encapsulated within a hydrogel bead may be used for combinatorial indexing of the single cells, for example, using a contiguity preserving transposition (CPTSeq) approach. In some embodiments, DNA from a single cell may be barcoded by encapsulation of single cells after WGA amplification with another bead carrying barcoded transposons and dissolving the gel matrix by contacting it with a reducing agent, for example, to release genomic DNA for barcoding.

Embodiments of the "spatial indexing" methods and techniques described herein shortens data analysis and simplifies the process of library preparation from single cells and long DNA molecules. Existing protocols for single cell sequencing requires efficient physical separation of the cells and uniquely barcoding each isolated cell and pooling everything back together to do sequencing. Current protocols for synthetic long reads also requires cumbersome barcoding steps, and pooling each barcoded fragments together for sequencing and letting data analysis to distinguish genetic information coming from each barcoded cell. During these long processes there is also loss of genetic material which causes dropouts in the sequences. Embodiments described herein not only shorten the process but also increase data resolution for single cells. Furthermore, embodiments provided herein simplify the assembly of genomes of new organisms. Embodiments described herein may be used to reveal rare genetic variations and co-occurrence of mutations. In some embodiments, DNA library confined in the hydrogel beads until release provide the opportunity to control the size of the fragments that is released on the surface by controlling the release process and hydrogel formulation.

In some embodiments, the surface is a flow cell device. In some embodiments, the flow cell is a custom flow cell device having wells, grooves, or patterns. In some embodiments, the flow cell comprises a patterned surface. In some embodiments, the patterned surface comprises wells. In some embodiments, the wells are from about 10 μm to about 50 μm in diameter, such as 10 μm, 15 μm, 20 μm, 25 μm, 30 μm, 35 μm, 40 μm, 45 μm, or 50 μm in diameter, or within a range defined by any two of the aforementioned values, and wherein the wells are about 0.5 μm to about 1 μm in depth, such as 0.5 μm, 0.6 μm, 0.7 μm, 0.8 μm, 0.9 μm, or 1 μm in depth, or within a range defined by any two of the aforementioned values. In some embodiments, the wells are comprised of hydrophobic material. In some embodiments, the hydrophobic material comprises an amorphous fluoropolymer, such as CYTOP, Fluoropel®, or Teflon®.

In some embodiments, the library may be amplified using primer sites in the adaptor sequences, and sequenced using sequencing primer sites in the adaptor sequences. In some embodiments the adaptor sequences can include indexes to identify the source of the nucleic acids. The efficiency of subsequent amplification steps can be reduced by the formation of primer-dimers. To increase the efficiency of subsequent amplification steps, non-ligated single-stranded adaptors can be removed from ligation products.

Preparing Nucleic Acid Libraries with Hydrogel Beads

Some embodiments of the systems, methods and compositions provided herein include methods in which adaptors are ligated to target nucleic acids. Adaptors can include sequencing primer binding sites, amplification primer binding sites, and indexes. For example, an adaptor can include a P5 sequence, a P7 sequence, or a complement thereof. As used herein a P5 sequence comprises a sequence defined by SEQ ID NO: 1 (AATGATACGGCGACCACCGA) and a P7 sequence comprises a sequence defined by SEQ ID NO: 2 (CAAGCAGAAGACGGCATACGA). In some embodiments, the P5 or P7 sequence can further include a spacer polynucleotide, which may be from 1 to 20, such as 1 to 15, or 1 to 10, nucleotides, such as 2, 3, 4, 5, 6, 7, 8, 9, or 10 nucleotides in length. In some embodiments, the spacer includes 10 nucleotides. In some embodiments, the spacer is a polyT spacer, such as a 10T spacer. Spacer nucleotides may be included at the 5' ends of polynucleotides, which may be attached to a suitable support via a linkage with the 5' end of the polynucleotide. Attachment can be achieved through a sulphur-containing nucleophile, such as phosphorothioate, present at the 5' end of the polynucleotide. In some embodiments, the polynucleotide will include a polyT spacer and a 5' phosphorothioate group. Thus, in some embodiments, the P5 sequence is 5'phosphorothioate-TTTTTTTTTTAATGATACGGCGACCACCGA-3' (SEQ ID NO: 3), and in some embodiments, the P7 sequence is 5'phosphorothioate-TTTTTTTTTTCAAGCAGAAGACGGCATACGA-3' (SEQ ID NO: 4).

Indexes can be useful to identify the source of a nucleic acid molecule. In some embodiments, an adaptor can be modified to prevent the formation of concatemers, for example by the addition of blocking groups that prevent extension of the adaptor at one or both ends. Examples of 3' blocking groups include a 3'-spacer C3, a dideoxynucleotide, and attachment to a substrate. Examples of 5' blocking groups include a dephosphorylated 5' nucleotide, and attachment to a substrate.

Adaptors include nucleic acids, such as single-stranded nucleic acids. Adaptors can include short nucleic acids having a length less than, greater than, or equal to about 5 nucleotides, 10 nucleotides, 20 nucleotides, 30 nucleotides, 40 nucleotides, 50 nucleotides, 60 nucleotides, 70 nucleotides, 80 nucleotides, 90 nucleotides, 100 nucleotides, or a range between any two of the foregoing sizes. In some embodiments, the adaptors are of sufficient size to pass through the pores of the hydrogel beads. Target nucleic acids include DNA, such as genomic or cDNA; RNA, such as mRNA, sRNA or rRNA; or a hybrid of DNA and RNA. The nucleic acid can be isolated from a single cell encapsulated within a hydrogel bead. A nucleic acid can contain phosphodiester bonds, and can include other types of backbones, comprising, for example, phosphoramide, phosphorothioate, phosphorodithioate, O-methylphosphoroamidite and peptide nucleic acid backbones and linkages. A nucleic acid can contain any combination of deoxyribo- and ribonucleotides, and any combination of bases, including uracil, adenine, thymine, cytosine, guanine, inosine, xanthanine, hypoxanthanine, isocytosine, isoguanine, and base analogs such as nitropyrrole (including 3-nitropyrrole) and nitroindole (including 5-nitroindole). In some embodiments, a nucleic acid can include at least one promiscuous base. A promiscuous base can base-pair with more than one different type of base and can be useful, for example, when included in oligonucleotide primers or inserts that are used for random hybridization in complex nucleic acid samples such as genomic DNA samples. An example of a promiscuous base includes inosine that may pair with adenine, thymine, or cytosine. Other examples include hypoxanthine, 5-nitroindole, acylic 5-nitroindole, 4-nitropyrazole, 4-nitroimidazole and 3-nitropyrrole. Promiscuous bases that can base-pair with at least two, three, four or more types of bases can be used.

An example method includes dephosphorylating the 5' ends of target nucleic acids to prevent the formation of concatemers in subsequent ligation steps; ligating first adaptors to the 3' ends of the dephosphorylated targets using a ligase, in which the 3' ends of the first adaptors are blocked; re-phosphorylating of the 5' ends of the ligated targets; ligating a second adaptor to the 5' ends of the dephosphorylated targets using the single-stranded ligase, in which the 5' ends of the second adaptors are non-phosphorylated.

Another example includes partial digestion of the nucleic acid with a 5' exonuclease to form a double-stranded nucleic acid with single-stranded 3' overhangs. An adaptor containing a 3' blocking group can be ligated to the 3' ends of double-stranded nucleic acid with 3' overhangs. The double-stranded nucleic acid with 3' overhangs with ligated adaptors can be dehybridized to form single-stranded nucleic acids. An adaptor containing a non-phosphorylated 5' end can be ligated to the 5' end of the single-stranded nucleic acid.

Methods to dephosphorylate nucleic acids, such as the 5' nucleotide of a nucleic acid include contacting a nucleic acid with a phosphatase. Examples of phosphatases include calf intestinal phosphatase, shrimp alkaline phosphatase, antarctic phosphatase, and APEX alkaline phosphatase (Epicentre).

Methods to ligate nucleic acids include contacting nucleic acids with a ligase. Examples of ligases include T4 RNA ligase 1, T4 RNA ligase 2, RtcB ligase, *Methanobacterium* RNA ligase, and TS2126 RNA ligase (CIRCLIGASE).

Methods to phosphorylate nucleic acids, such as the 5' nucleotide of a nucleic acid include contacting a nucleic acid with a kinase. Examples of kinases include T4 polynucleotide kinase.

Embodiments provided herein relate to preparing nucleic acids libraries in a hydrogel bead, such that the nucleic acid library is prepared in a single reaction volume.

Embodiments of the systems and methods provided herein include kits, containing any one or more of the hydrogel polymers, crosslinkers, or microfluidic devices for preparing hydrogel beads that encapsulate genetic material, and further including components useful for processing of the genetic material, including reagents for cell lysis, and nucleic acid amplification and sequencing, or for nucleic acid library preparation, including lysozyme, proteinase K, random hexamers, polymerase (for example, Φ29 DNA polymerase, Taq polymerase, Bsu polymerase), transposase (for example, Tn5), primers (for example, P5 and P7 adaptor sequences), ligase, catalyzing enzyme, deoxynucleotide triphosphates, buffers, or divalent cations as described herein, and as used for the respective processing of genetic material.

EXAMPLES

Example 1-Preparation of Hydrogel Beads

The following example demonstrates an embodiment of preparing hydrogel beads encapsulating long DNA fragments using microfluidic droplet generators.

A droplet generator was used to generate the hydrogel beads. Samples containing long DNA fragments were mixed with polymer precursor and the mixture was loaded into a sample reservoir on a cartridge. Within 2 minutes, around 50,000 hydrogel beads containing long DNA were generated from each channel (8 channels for 8 independent sample processing each cartridge. The long DNA hydrogel beads were loaded onto a flow cell, where hydrogel beads stuck inside (100 μm high channel and 120 μm hydrogel beads diameter) for hands-free library preparation. The Nextera enzymes and reagents contact the flow cell, contacting the long DNA embedded inside the hydrogel bead, forming a library. The library was then seeded on the flow cell. During library seeding, oil was loaded to fill the void between beads and the flow cell was heated to accelerate diffusion of the library. In the presence of the oil, seeding occurred in close proximity to the footprint of each hydrogel bead (from 120 μm diameter hydrogel beads, library seeding is limited to a roughly 120 μm diameter area).

Long DNA molecules were loaded and trapped in hydrogel beads (about 120 μm in diameter) and library preparation was directly performed on these long DNA molecules embedded inside the hydrogel beads. As a result, all DNA libraries from a specific long DNA molecule were stored within the same hydrogel beads. The library was then released from the hydrogel beads to the flow cell surface to seed them as a group on the flow cell surface. The clusters released from a long DNA molecule grouped together as a "cluster patch" on the flow cell. Clusters inside a single patch from a single long DNA molecule simplifies reconstruction of the genome with higher accuracy and fewer scaffolding gaps.

Example 2-Long DNA Spatial Indexing

Figure 3:
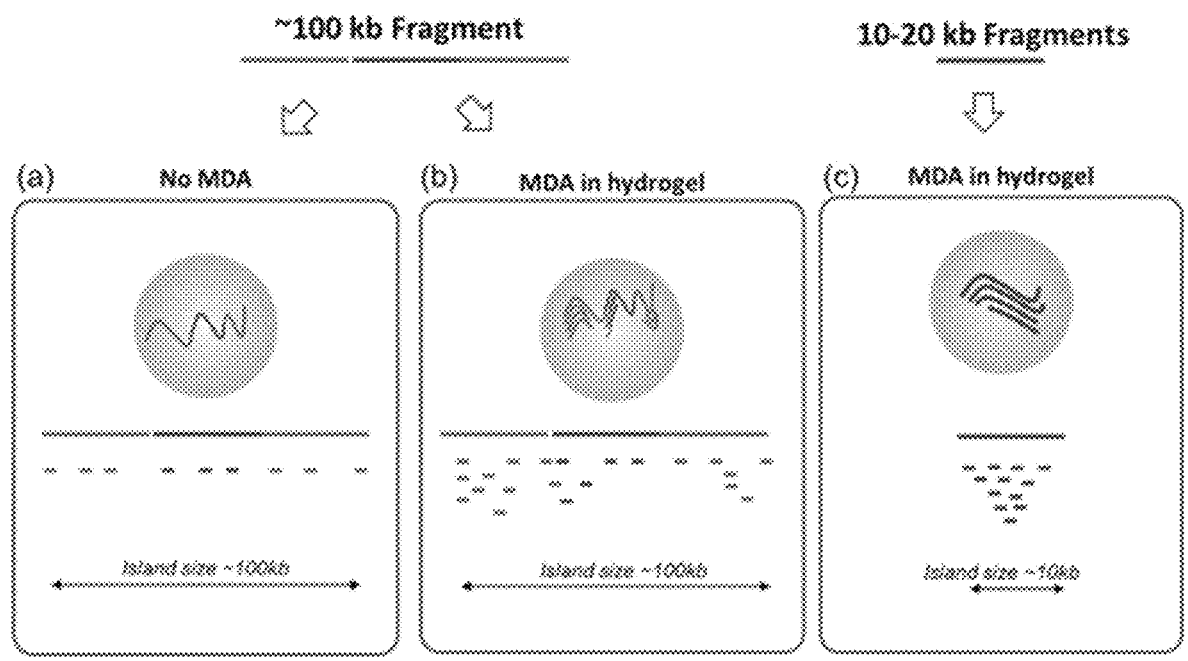
FIG. 3 is a schematic that illustrates workflow of DNA sequencing of long DNA encapsulated within hydrogel beads, including DNA fragments of about 100 kb (without a multiple displacement amplification (MDA) step (panel (a)) or with an MDA step (panel (b)) prior to tagmentation) and DNA fragments of about 10-20 kb (panel (c)).

The following example demonstrates an embodiment of strobed reads of long DNA fragment of 100 kb encapsulated within a hydrogel bead with or without MDA, as outlined in FIG. 3.

Figure 4:
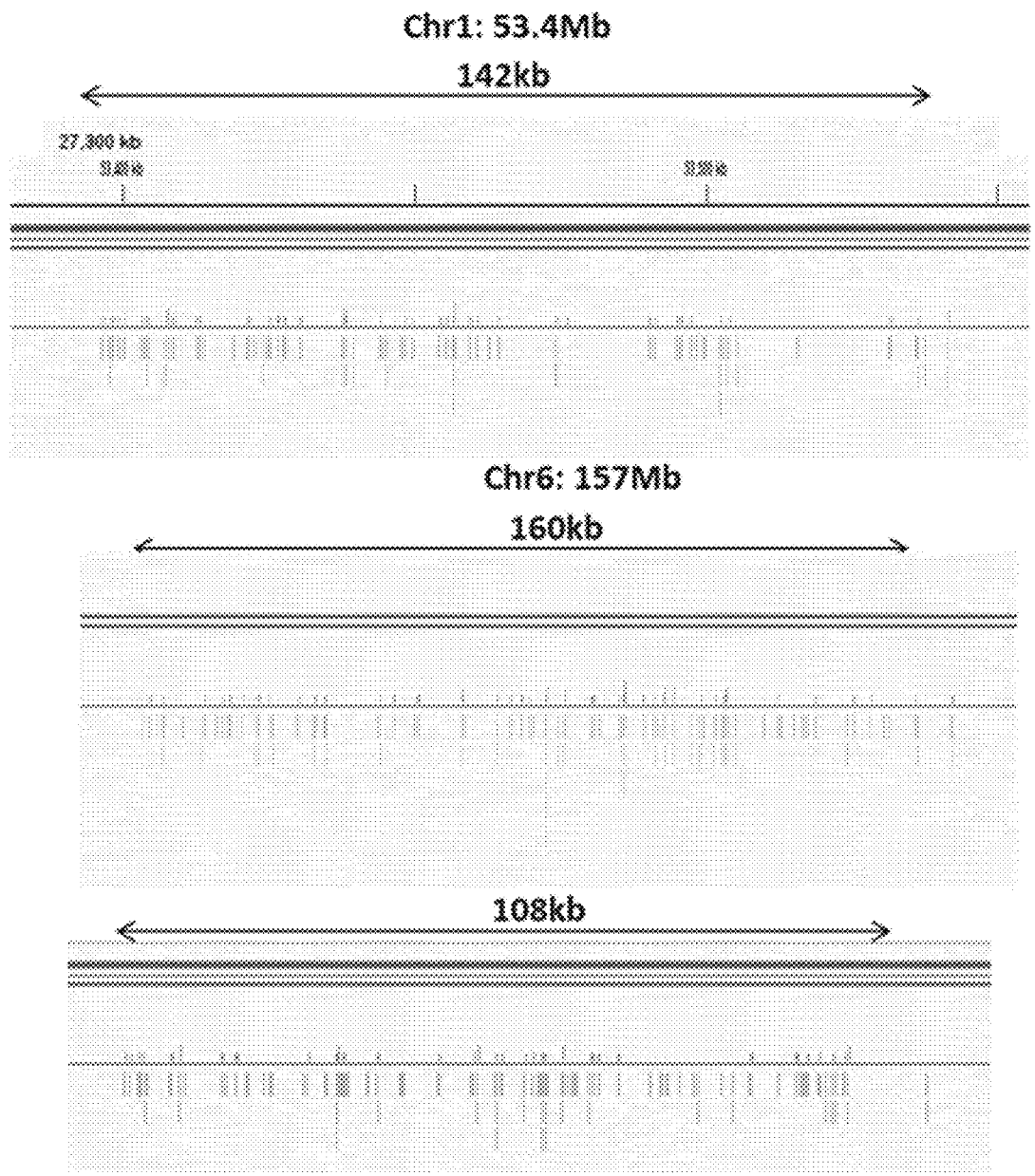
FIG. 4 is a graph that depicts strobed reads of long DNA hydrogel spatial indexing sequencing data from a 100 kb DNA fragment without MDA.
Figure 5:
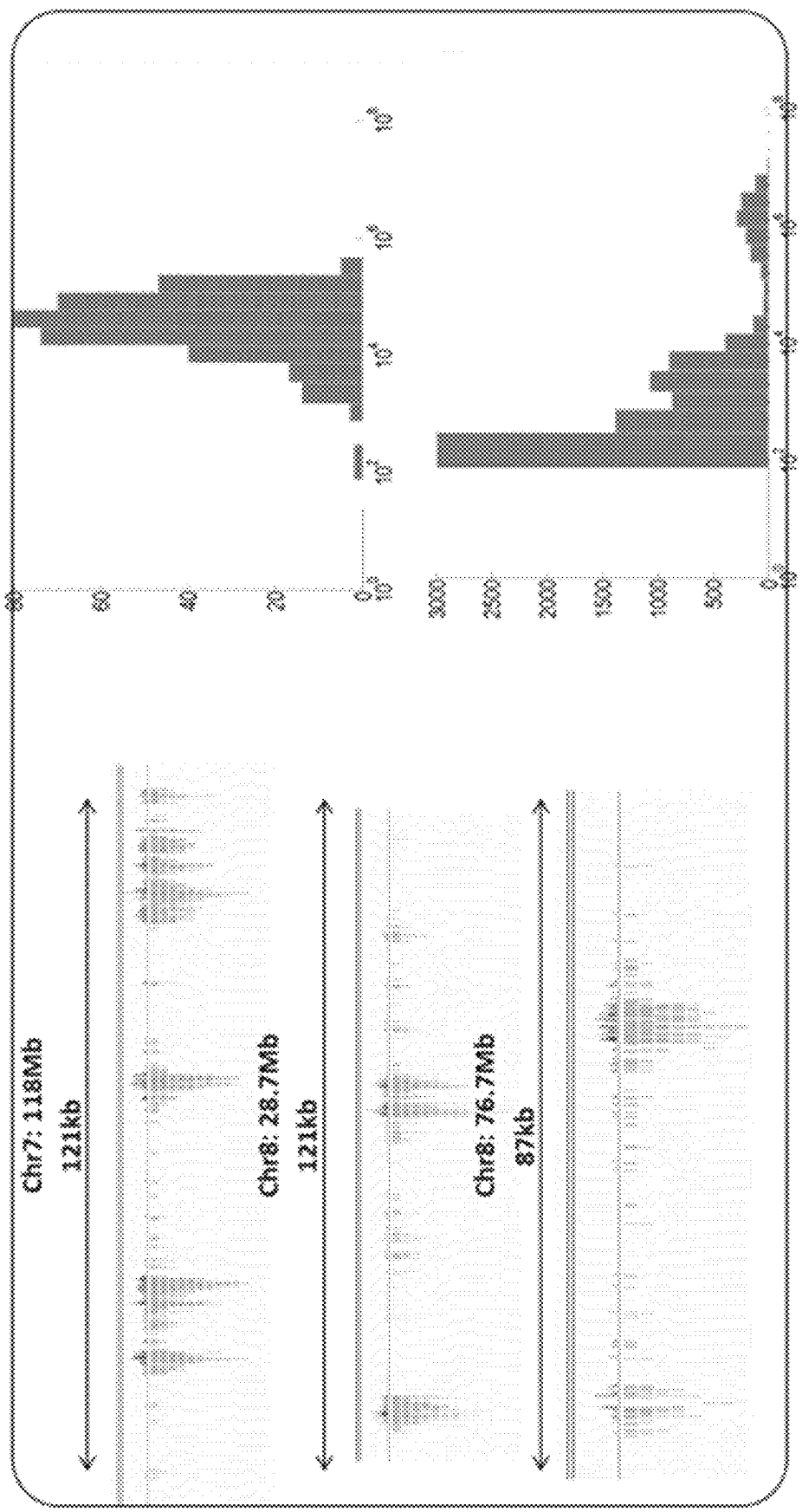
FIG. 5 shows a line graph of linked reads of long DNA hydrogel spatial indexing on 100 kb DNA fragments with MDA.

Hydrogel beads were prepared by mixing a polymer in the presence of Corriell genomic DNA of about 100 kb and forming hydrogel beads using a microdroplet generator. The DNA was subjected to spatial indexing sequencing by placing the formed hydrogel beads encapsulating the DNA fragments on a flow cell device, and contacting the flow cell with reagents. No MDA was performed. Results are shown in FIG. 4. The beads were degraded and clusters formed on the flow cell device. As shown in FIG. 5, the average clusters per long DNA island was about 33, the average long DNA island size was 64000 base pairs, and there were about 405 long DNA islands per bead.

Figure 6:
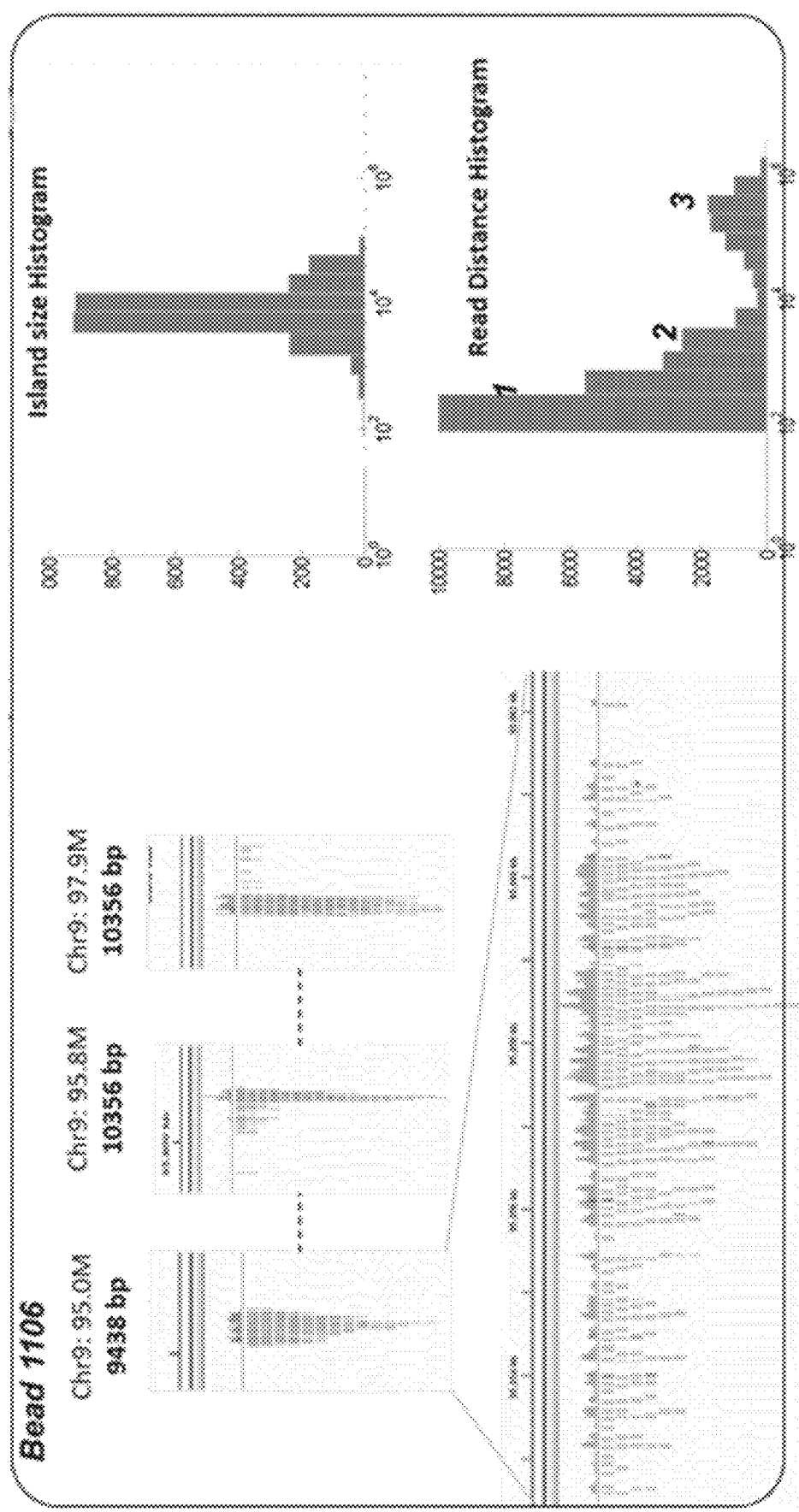
FIG. 6 shows a line graph of linked reads of long DNA hydrogel spatial indexing on 10 kb DNA fragments with MDA.

A second set of hydrogel beads were prepared by mixing a polymer in the presence of Corriell genomic DNA of about 100 kb and forming hydrogel beads using a microdroplet generator. The DNA was subjected to spatial indexing sequencing by placing the formed hydrogel beads encapsulating the DNA fragments on a flow cell device, and contacting the flow cell with reagents. MDA was performed prior to tagmentation. The beads were degraded and clusters formed on the flow cell device. As shown in FIG. 6, the average clusters per long DNA island increased to about 85, the average long DNA island size was 58000 base pairs, and there were about 166 long DNA islands per bead.

A third set of hydrogel beads were prepared by mixing a polymer in the presence of Corriell genomic DNA of about 10 kb and forming hydrogel beads using a microdroplet generator. The DNA was subjected to spatial indexing sequencing by placing the formed hydrogel beads encapsulating the DNA fragments on a flow cell device, and contacting the flow cell with reagents. MDA was performed prior to tagmentation. The beads were degraded and clusters formed on the flow cell device. As shown in FIGS. 7A-7B, the average clusters per long DNA island was about 57, the average long DNA island size was 10461 base pairs, and there were about 85 long DNA islands per bead.

Example 3-Metagenomics on Complex Mixture of Microbial Species

The following example demonstrates an embodiment of identifying single cell microbes encapsulated within a hydrogel.

Figure 8:
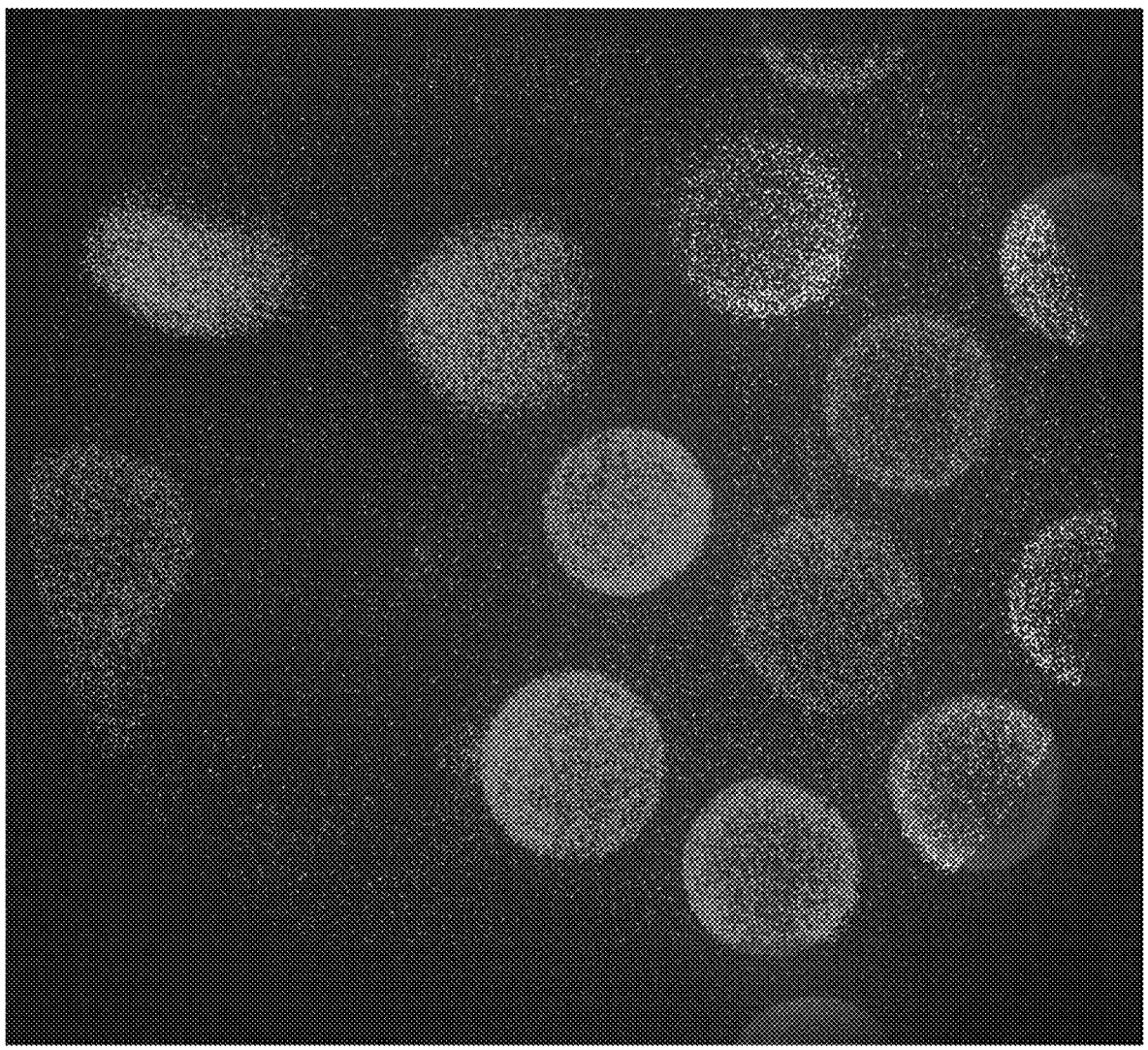
FIG. 8 depicts a micrograph showing identification of microbial species encapsulated within a hydrogel bead. The hydrogel bead encapsulated various microbial species, and spatial sequencing reads were performed to identify the microbes.
Figure 9:
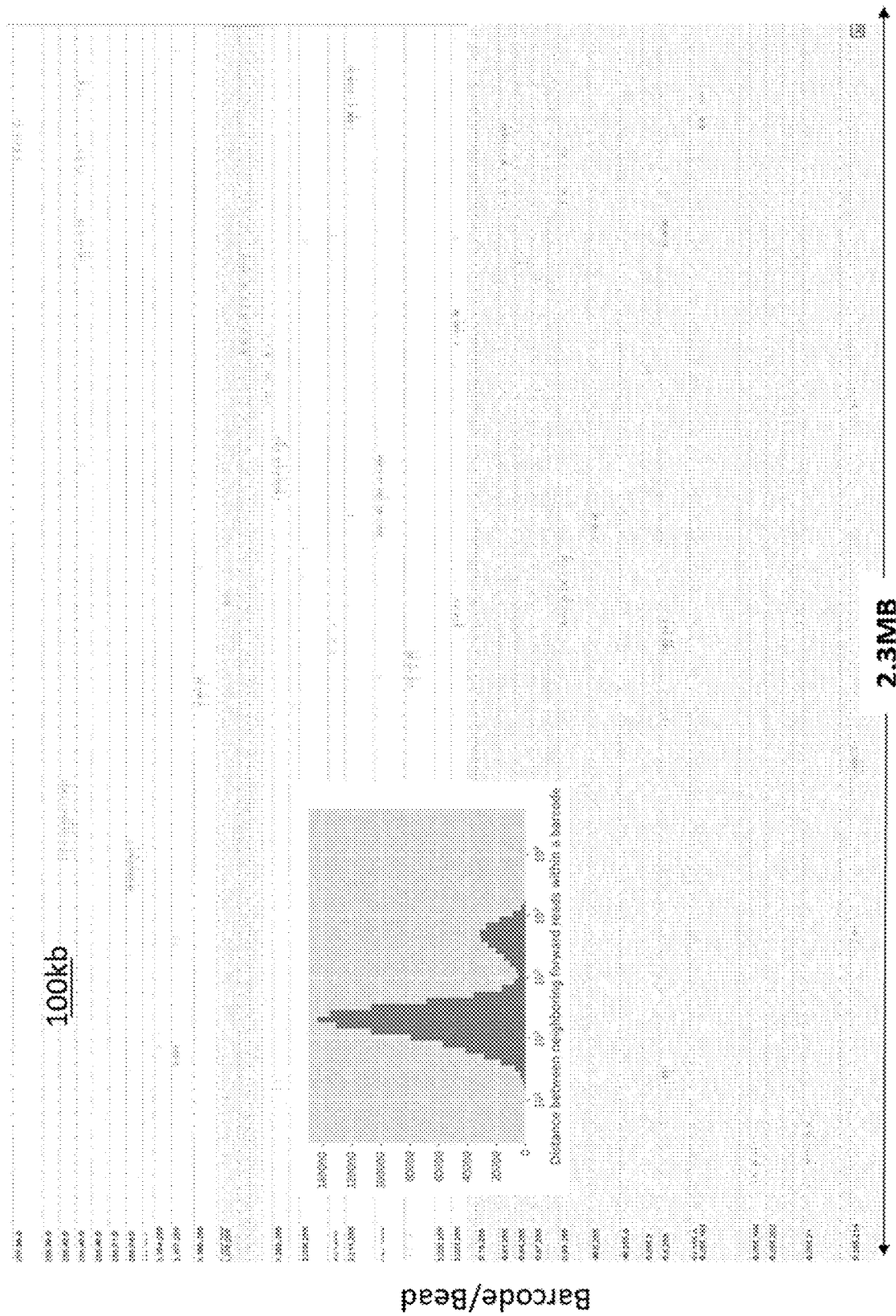
FIG. 9 illustrate a graph showing the distribution of barcode reads for long DNA encapsulating within hydrogel beads.

Hydrogel beads were prepared as described herein using a microfluidics microdroplet generator. The polymer material was mixed with a sample containing a number of microbes, including *L. gasseri, S. aureus, B. cereus, B. vulgatus, A. baumannii, S. agalactiae,* and *P. acnes.* The encapsulated cells were then lysed and subjected to library preparation, whereupon the hydrogel beads were degraded and the libraries deposited on a surface. Micrographs depict hydrogel bead encapsulated various microbial species, and spatial sequencing reads were performed to identify the microbes, as shown in FIG. 8. As shown in FIG. 9, each microbe was capable of being identified due to its spatial compartmentalization on the flow cell device. Thus, the encapsulating and subsequent nucleic acid reactions enable strain-level identification of microbial species in complex mixtures using reads compartmentalization in a mini-metagenomics assay.

Figure 10A:
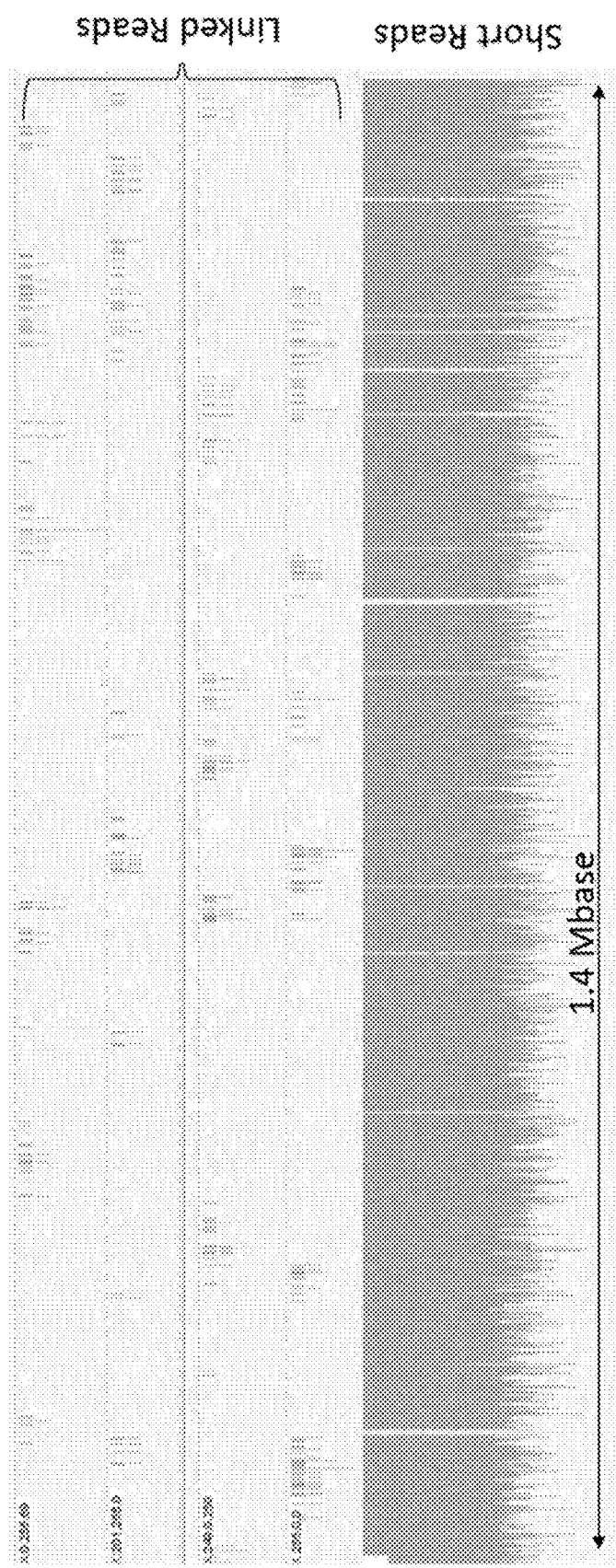
FIG. 10A illustrates a graph showing short reads and linked reads from a single run for an E. coli cell encapsulated within a hydrogel bead. As shown in the figure, linked reads span across repeat regions, and can improve de novo sequence assembly.
Figure 10B:
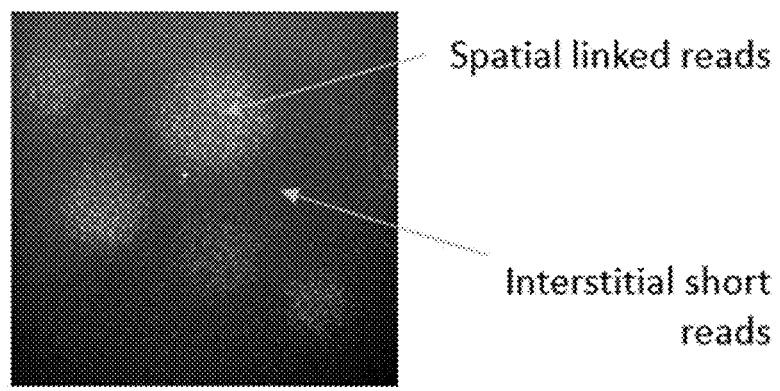
FIG. 10B shows a micrograph depicting spatial linked reads and interstitial short reads.

As shown in FIG. 10A, short reads and linked reads were obtained. from a single run for an *E. coli* cell encapsulated within a hydrogel bead. The linked reads span across repeat regions, and can improve de novo sequence assembly. As shown in FIG. 10B, micrograph depict spatial linked reads and interstitial short reads.

Example 4-On Flow Cell Spatial Indexing

The following example demonstrates an embodiment for on-flow cell spatial indexing.

A flow cell device was obtained and washed with 200 µl PR2. Beads for processing were also washed with PR2. A diluted hydrogel was prepared in PR2. Increased dilution results in increased spacing between hydrogels. The hydrogel was embedded on the flow cell, and the introduction of air bubbles to the flow cell was avoided. 200 µl PR2 was flowed through the flow cell to ensure beads remained fixed to go through the process. 100 µl RSB was flowed through the flow cell.

A tagmentation mix was prepared by mixing 25 µl tagmentation reagent, 23 µl RSB, and 2 µl enzyme. The tagmentation mix was introduced to the narrow channel to remove any possible air bubble on the inlet. The tagmentation mix was then flowed slowly to the inlet. The flow cell was sealed and incubated for 10 min at 55° C.

A stop buffer mix was prepared by mixing 25 µl tagmentation buffer, 25 µl RSB, and 10 µl stop buffer. The stop buffer mix was slowly flowed onto the flow cell without introducing any bubbles, and incubated at room temperature for 5 minutes. After incubation, 200 µl of PR2 was flowed through the device.

NPM was prepared by mixing 175 µl RSB and 75 µl NPM. The NPM mix was slowly flowed onto the flow cell device without introducing any air bubble, and incubated for 3 minutes at room temperature. 200 µl of oil with surfactant was flowed onto the flow cell device. Micrographs revealed that the hydrogels were surrounded with NPM mix and oil. The flow cell was sealed and incubated for 3 minutes at 72° C. for gap filling reaction.

20-30 µl of oil with surfactant and oil with DTT (29/2 ratio) were flowed onto the flow cell device, and the device was sealed. The start temperature release process was 90° C. for 3 minutes, 60° C. for 5 minutes, 40° C. for 2 minutes, and 20° C. for 2 minutes. The flow cell was washed with 400 µl PR2, and 200 µl CLM. The flow cell was then washed with 400 µl PR2. Where phix seeding is desired, a Phix was prepared with 2-3 µM concentration, and the phix library was flowed onto the device, and incubated at room temperature for 5 mins. The flow cell was washed with 200 µl PR2. 100-200 µl AMX for 1st extension was flowed, and incubated for 5 minutes at 50° C. The flowcell was washed with PR2, and a 24 or 30 cycle amplification was performed The embodiments, examples, and figures described herein provide compositions, methods, and systems for retaining genetic material in physically confined space during the process from lysis to library generation. Some embodiments provide libraries originated from single long DNA molecule or a single cell to be released on a surface of a flow cell in confined space. Once the library from a single DNA molecule or single cell in the individual compartments are released to the surface of the flow cell, the library from each compartment gets seeded at close proximity to each other.

The term "comprising" as used herein is synonymous with "including," "containing," or "characterized by," and is inclusive or open-ended and does not exclude additional, unrecited elements or method steps.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A hydrogel bead for performing DNA reactions, comprising:
    a hydrogel polymer precursor, wherein the hydrogel polymer precursor is polyacrylamide;
    a reversible polymer crosslinker that degrades in the presence of a reducing agent, wherein the reversible polymer crosslinker is N,N'-bis(acryloyl)cystamine (BACy); and
    DNA disposed within the hydrogel bead, wherein the bead comprises pores that allow diffusion of a reagent through the bead while retaining the DNA.

2. The bead of claim 1, wherein the bead has a diameter of about 50 µm to about 150 µm.

3. The bead of claim 1, wherein the DNA is a long DNA molecule of 50,000 base pairs or greater.

4. The bead of claim 1, wherein the reagent comprises enzymes, chemicals, and primers having a size of less than 50 base pairs.

5. The bead of claim 1, wherein the reagent comprises lysozyme, proteinase K, random hexamers, polymerase (Φ29 DNA polymerase, Taq polymerase, Bsu polymerase), transposase (Tn5), primers (P5 and P7 adaptor sequences), ligase, catalyzing enzyme, deoxynucleotide triphosphates, buffers, or bivalent cations.

6. A flow cell device for performing DNA sequencing, comprising:
a solid support comprising a surface having a degradable hydrogel bead of claim 1 encapsulating DNA deposited thereon, wherein the degradable hydrogel bead comprises pores that are sized to allow diffusion of a reagent through the hydrogel, but are too small to allow DNA to traverse the pores.

7. The flow cell device of claim 6, wherein the solid support is functionalized with a surface polymer.

8. The flow cell device of claim 7, wherein the surface polymer is poly(N-(5-azidoacetamidylpentyl) acrylamide-co-acrylamide) (PAZAM) or silane free acrylamide (SFA).

9. The flow cell device of claim 6, wherein the flow cell comprises a patterned surface.

10. The flow cell device of claim 9, wherein the patterned surface comprises wells.

11. The flow cell device of claim 10, wherein the wells are from about 10 µm to about 50 µm in diameter, such as 10 µm, 15 µm, 20 µm, 25 µm, 30 µm, 35 µm, 40 µm, 45 µm, or 50 µm in diameter, or within a range defined by any two of the aforementioned values, and wherein the wells are about 0.5 µm to about 1 µm in depth, such as 0.5 µm, 0.6 µm, 0.7 µm, 0.8 µm, 0.9 µm, or 1 µm in depth, or within a range defined by any two of the aforementioned values.

12. The flow cell device of claim 9, wherein the wells are comprised of hydrophobic material.

13. The flow cell device of claim 12, wherein the hydrophobic material comprises an amorphous fluoropolymer, such as CYTOP, Fluoropel®, or Teflon®.

14. The flow cell device of claim 6, wherein the hydrogel bead has a diameter of about 50 pm to about 150 pm.

15. The flow cell device of claim 6, wherein the DNA is a long DNA molecule of 50,000 base pairs or greater.

16. The flow cell device of claim 6, wherein the reagent comprises enzymes, chemicals, and primers having a size of less than 50 base pairs.

17. The flow cell device of claim 6, wherein the reagent comprises lysozyme, proteinase K, random hexamers, polymerase (Φ29 DNA polymerase, Taq polymerase, Bsu polymerase), transposase (Tn5), primers (P5 and P7 adaptor sequences), ligase, catalyzing enzyme, deoxynucleotide triphosphates, buffers, or divalent cations.

18. A system for DNA sequencing, comprising:
a stage configured to hold a flow cell device of claim 6;
a flow cell device of claim 6; and
a detector for obtaining sequencing data.

19. A method of sequencing DNA comprising:
obtaining a bead encapsulating DNA of claim 1;
amplifying DNA encapsulated within the hydrogel;
performing a tagmentation reaction on the DNA encapsulated within the hydrogel; and
sequencing the DNA,
thereby generating a DNA library encapsulated within the hydrogel.

20. The method of claim 19, wherein the DNA is a long DNA molecule of 50,000 base pairs or greater.

21. The method of claim 19, further comprising performing a DNA amplification reaction on DNA encapsulated within the hydrogel prior to performing the tagmentation reaction.

22. The method of claim 21, wherein the DNA amplification reaction comprises multiple displacement amplification (MDA).

23. The method of claim 19, wherein the tagmentation reaction comprises contacting genetic material with a transposase mixture comprising adapter sequences and transposomes.

24. The method of claim 19, further comprising seeding the DNA library on a solid support.

25. The method of claim 24, wherein seeding comprises cleaving the hydrogel to release the DNA library from the hydrogel.

26. The method of claim 25, wherein the hydrogel is cleaved by contacting the hydrogel with a cleavage mix or by heating the hydrogel to about 90° C. to release the DNA library.

27. The method of claim 26, wherein the cleavage mix comprises dithiothreitol (DTT), tris(2-carboxyethyl)phosphine (TCEP), or tris(3-hydroxypropyl)phosphine (THP).

28. The method of claim 24, wherein the solid support is a flow cell device.

29. The bead of claim 1, wherein the reducing agent is dithioerythritol (DTE), dithiothreitol (DTT), 2-mercaptoethanol or 3-mercaptoethanol (BME), 2-mercaptoethanol, glutathione, thioglycolate, 2,3-dimercaptopropanol, tris(2-carboxyethyl)phosphine (TCEP), tris(hydroxymethyl)phosphine (THP), or P-[tri s(hydroxymethyl)phosphine] propionic acid (THPP).

* * * * *

```
                        SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 1
aatgatacgg cgaccaccga                                              20

<210> SEQ ID NO 2
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 2
caagcagaag acggcatacg a                                            21

<210> SEQ ID NO 3
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 3
tttttttttt aatgatacgg cgaccaccga                                   30

<210> SEQ ID NO 4
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 4
tttttttttt caagcagaag acggcatacg a                                 31
```